(12) United States Patent
Yang et al.

US009475790B2

(10) Patent No.: US 9,475,790 B2
(45) Date of Patent: Oct. 25, 2016

(54) METHOD FOR PREPARING REFINED LACTIDE FROM RECOVERED POLYLACTIC ACID

(71) Applicant: Xiaogan Esun New Material Co., Ltd., Xiaogan (CN)

(72) Inventors: Yihu Yang, Xiaogan (CN); Jie Xu, Xiaogan (CN)

(73) Assignee: XIAOGAN ESUN MATERIAL CO., LTD., Xiaogan (CN)

( * ) Notice: Subject to any disclaimer, the term of this patent is extended or adjusted under 35 U.S.C. 154(b) by 0 days.

(21) Appl. No.: 14/534,151

(22) Filed: Nov. 5, 2014

(65) Prior Publication Data

US 2015/0065732 A1 Mar. 5, 2015

Related U.S. Application Data

(63) Continuation-in-part of application No. PCT/CN2012/077930, filed on Jun. 29, 2012.

(51) Int. Cl.
*C07D 319/00* (2006.01)
*C07D 319/12* (2006.01)
*C08J 11/12* (2006.01)
*C08J 11/16* (2006.01)

(52) U.S. Cl.
CPC .............. *C07D 319/12* (2013.01); *C08J 11/12* (2013.01); *C08J 11/16* (2013.01); *C08J 2367/04* (2013.01); *Y02W 30/703* (2015.05); *Y02W 30/705* (2015.05)

(58) Field of Classification Search
CPC ........ B22F 2998/10; B22F 3/02; B22F 3/15; B22F 9/04; C07D 319/12; C04B 2235/3839; C04B 2235/3843; C04B 2235/404; C04B 2235/405; C04B 2235/422; C04B 2235/5436; C04B 2235/5445; C04B 2235/6581; C04B 2235/785; C04B 2235/96; C04B 35/5626; C04B 35/6455; C08J 11/10; C08J 11/12; C08J 11/16; C22C 29/08; Y02W 30/703; Y02W 30/705
See application file for complete search history.

(56) References Cited

U.S. PATENT DOCUMENTS

| | | | | |
|---|---|---|---|---|
| 4,379,525 A | * | 4/1983 | Nowicki | B03B 9/061 241/101.8 |
| 5,728,847 A | * | 3/1998 | Ohara | C07D 319/12 549/274 |
| 6,326,458 B1 | * | 12/2001 | Gruber | C07D 319/12 525/415 |

FOREIGN PATENT DOCUMENTS

| | | | |
|---|---|---|---|
| CN | 1429814 | * | 7/2003 |
| JP | 6-256340 | * | 9/1994 |

OTHER PUBLICATIONS 340 translated 1994.*
814 translated 2003.*

* cited by examiner

*Primary Examiner* — Yevegeny Valenrod
*Assistant Examiner* — Blaine G Doletski
(74) *Attorney, Agent, or Firm* — Matthias Scholl, PC; Matthias Scholl

(57) ABSTRACT

A method for preparing lactide from recovered polylactic acid, the method including the following steps: A. pretreating the recovered polylactic acid; B. extruding the treated polylactic acid from a twin screw extruder to yield a polylactic acid melt, and introducing the polylactic acid melt to a pre-depolymerization kettle; C. carrying out a chain scission reaction to break molecular chains in the polylactic acid melt and to decrease the number-average molecular weight of the polylactic acid melt to below 5000; D. conducting depolymerization reaction to yield a crude lactide; and E. purifying the crude lactide and crystallizing the purified lactide.

11 Claims, No Drawings

METHOD FOR PREPARING REFINED LACTIDE FROM RECOVERED POLYLACTIC ACID

CROSS-REFERENCE TO RELATED APPLICATIONS

This application is a continuation-in-part of International Patent Application No. PCT/CN2012/077930 with an international filing date of Jun. 29, 2012, designating the United States, now pending, the contents of which, including any intervening amendments thereto, are incorporated herein by reference. Inquiries from the public to applicants or assignees concerning this document or the related applications should be directed to: Matthias Scholl P.C., Attn.: Dr. Matthias Scholl Esq., 245 First Street, 18th Floor, Cambridge, Mass. 02142.

BACKGROUND OF THE INVENTION

1. Field of the Invention

The invention relates to a method for preparing lactide from recovered polylactic acid.

2. Description of the Related Art

Lactide is a natural, renewable, and biodegradable compound and is primarily used in the production of polylactic acid by ring-opening polymerization. Conventional methods for making polylactic acid produce a large amount of byproducts, which have no use and must be disposed of.

SUMMARY OF THE INVENTION

In view of the above-described problems, it is one objective of the invention to provide a method for preparing a refined lactide from recovered polylactic acid. The method utilizes recovered polylactic acid as a raw material and adopts pretreatment of raw materials, melting, chain scission, depolymerization, and purification processes to produce a refined lactide having a purity of 99.5 wt. % and an optical purity exceeding 99.5%.

To achieve the above objective, in accordance with one embodiment of the invention, there is provided a method for preparing lactide from recovered polylactic acid, the method comprising the following steps:

A. pretreatment of raw materials: breaking recovered polylactic acid by a crusher, washing and filtrating the polylactic acid to remove impurities, and desiccating the polylactic acid to remove water;

B. melting: transporting the polylactic acid after the pretreatment step to a hopper of a twin screw extruder, extruding the treated polylactic acid from the twin screw extruder to yield a polylactic acid melt, and introducing the polylactic acid melt to a pre-depolymerization kettle;

C. chain scission: stirring the polylactic acid melt in the presence of a catalyst at a temperature of between 180 and 250° C. for carrying out the chain scission reaction so as to break a molecular chain of the polylactic acid melt and to decrease a number-average molecular weight of the polylactic acid melt to below 5000;

D. depolymerization: transporting the polylactic acid melt after the chain scission to a depolymerization system via a first delivery pump, and conducting depolymerization reaction at a temperature of between 150 and 250° C. and at a vacuum of between 0.1 and 0.09 MPa to yield a crude lactide; and E. purification: transporting the crude lactide to a purification system via a second delivery pump, and crystallizing the purified lactide, whereby yielding a refined lactide.

In a class of this embodiment, the recovered polylactic acid is selected from the group consisting of a substandard polylactic acid, an unqualified polylactic acid, a waste sheet of the polylactic acid, and a waste film material of the polylactic acid, a waste product of the polylactic acid, and scraps produced in processing polylactic acid products, and a mixture thereof. The recovered polylactic acid in the pre-treatment of the raw materials is broken into particles of between 3 and 4 cm. A water content of the recovered polylactic acid in the pre-treatment of the raw materials is controlled at 0.1 wt. % below.

In a class of this embodiment, the catalyst added in the chain scission reaction is selected from the group consisting of a zinc catalyst, a tin catalyst, an organic catalyst, or a mixture thereof. The catalyst accounts for between 1/10000 and 100/10000 of the polylactic acid melt by weight. The catalyst is selected from the group consisting of zinc lactate, zinc oxide, zinc dust, diethyl zinc, tin lactate, tin oxide, tin dioxide, stannous oxide, stannous lactate, stannous octoate, stannous chloride, tin powder, propionic acid, butyl titanate, and a composite catalyst thereof. Preferably, the lactide is a composite catalyst comprising zinc lactate, stannous oxide, and butyl titanate at a weight ratio of 1:1:1, or a composite catalyst comprising zinc lactate, zinc dust, and propionic acid at a weight ratio of 1:2:1.

In a class of this embodiment, the chain scission reaction in step C) lasts for between 1 and 5 hr, preferably 3 hr. The number-average molecular weight of the polylactic acid melt after the chain scission reaction in step C) is decrease to between 2000 and 3000.

In a class of this embodiment, the depolymerization system in step D) comprises: a circulating pump, a horizontal depolymerization kettle, and a wiped film evaporator.

The temperature of materials in the depolymerization reaction is controlled at between 180 and 220° C., preferably at 200° C. The vacuum degree in the depolymerization reaction in step D) is controlled at between 0.1 and 0.098 MPa.

In a class of this embodiment, a content of L-lactide accounts for over 85 wt. % of the crude lactide obtained from the depolymerization reaction in step D), and the content of D-lactide accounts for less than 2 wt. %.

In a class of this embodiment, a melt crystallization device in step E) comprises: a circulating pump, a dual falling film melt crystallizer, and a lactide tank. The refined lactide obtained from the melt crystallization of the crude lactide in step E) has a lactide content exceeding 99.5 wt. % and an optical purity exceeding 99.5%.

Advantages according to embodiments of the invention are summarized as follows:

1. Different from the conventional methods, the method of the invention utilizes recovered polylactic acid rather than lactic acid as the raw material. The method of the invention does not require desiccation and polycondensation processes, thereby simplifying the production procedure. The whole production process neither requires water nor produces waste water. Besides, the raw materials are completely utilized, and the three-waste emission hardly occurs, thereby being environmentally friendly.

2. As a chemical method for recovering the polylactic acid materials, the method of the invention combines a small cycle with the natural cycle for recovering the polylactic acid materials, so that the natural resource is completely utilized, which is beneficial to decreasing the environment pollution and the carbon emission.

3. The polylactic acid is conducted with the chain scission treatment after the melting process so as to ensure that the molecular weight of the polylactic acid melt is between 2000 and 3000 before entering the depolymerization system. Not only is the homogeneity of the molecular weight of the raw material of the depolymerization ensured, but also the raw material is at the best sate for the progress of the depolymerization at the beginning of the depolymerization. It is also beneficial for a stable working condition of the depolymerization and a stable product quality, for the decrease of the temperature for carrying out the depolymerization reaction, as well as for the improvement of the unit output, decrease of the occurrence of the side reactions, and the increase of the product yield. The effective component in the crude lactide produced by the method of the invention accounts for exceeding 85 wt. %.

4. The wiped film evaporator is utilized as the depolymerization reactor. During the production, materials flow downward in a film state and lactide vapor flows upward within a cylinder body. Thus, the lactide vapor is prone to overflow from the polylactic acid melt, the detention time of lactide in the high temperature depolymerization system is decreased, the probability of the occurrence of side reactions of the lactide at high temperature is decreased, and the quality of the crude lactide is improved. Since the polylactic acid melt is always in a flowing state, the material is rapidly renewed, and the retention time thereof is shortened. Compared with the conventional kettle-type depolymerization device, the wiped film evaporator has a much higher heat transfer efficiency, a temperature of a heated heating medium is properly decreased, which effectively prevents the polylactic acid melt from coking at the high temperature and therefore improves the utilization of the raw material.

5. The purification of lactide adopts melt crystallization technology, and the separation of lactide is performed in the dual falling film crystallizer. The melt crystallization does not require any solvent and the dual falling film crystallizer has high efficiency, low energy consumption, and stable product quality. It is found from the conventional tests that the produced refined lactide has the content exceeding 99.5 wt. % and the optical purity exceeding 99.9%.

DETAILED DESCRIPTION OF THE EMBODIMENTS

For further illustrating the invention, experiments detailing method for preparing a refined lactide from recovered polylactic acid are described below. It should be noted that the following examples are intended to describe and not to limit the invention.

Example 1

A. Pretreatment of raw materials: a substandard polylactic acid material was broken into particles having a diameter of 3 cm by a crusher, washed and filtrated to remove impurities, and desiccated to remove water so as to control a water content to be below 0.1 wt. %.

B. Melting: the substandard polylactic acid after the pretreatment was transported to a hopper of a twin screw extruder. A melt was extruded from the twin screw extruder and introduced into a pre-depolymerization kettle for chain scission treatment to obtain a polylactic acid melt.

C. Chain scission: the polylactic acid melt was added with a catalyst comprising zinc lactate and zinc dust at a weight ratio of 1:1 at a temperature of 200° C., and a weight ratio of the catalyst to the polylactic acid melt was controlled at 1/10000. Chain scission reaction was performed in stirring condition to break the molecular chain of the polylactic acid melt. After 3 hr of reaction, the number-average molecular weight of the polylactic acid melt in the kettle was decreased to below 2300.

D. Depolymerization: the polylactic acid melt after the chain scission was transported to a depolymerization system via a first delivery pump, and depolymerization reaction was conducted at a temperature of 210° C. at a vacuum of 0.099 MPa to yield a crude lactide. A content of L-lactide in the crude lactide reaches 85 wt. %.

E. Purification: the crude lactide obtained from the depolymerization was transported to a melt crystallization system via a second delivery pump. A refrigerant circulating pump of a dual falling film crystallizer was started. A circulating pump of a crude lactide was started. The temperature was decreased from 100° C. to 60° C. at a rate of 5° C./hr by a refrigerant of the crystallizer, and lactide began to be crystallized in the crystallizer. The crystallization was finished when a crystallized lactide accounted for 80 wt. % of a total weight of the crude lactide. The circulating pump of the crude lactide was stopped, and an uncrystallized solution residue was discharged. The refrigerant circulating pump of the crystallizer was stopped, and a heating medium circulating pump was started. The temperature was increased from 60° C. to 95° C. at a rate of 5° C./hr by a heating medium of the crystallizer, and then sweating treatment was performed. When a sweating solution reached 10 wt. % of the crystallized lactide, the sweating treatment was finished, and the sweating solution was discharged. The temperature of the heating medium was increased to 100° C., and crystals in the crystallizer were totally melted and discharged. A product after the crystallization had a content of 99.6 wt. % and an optical purity of 99.9%.

Example 2

A. Pretreatment of raw materials: a waste sheet of the polylactic acid, a waste film material of the polylactic acid, and a waste product of the polylactic acid was broken into particles having a diameter of 4 cm by a crusher, washed and filtrated to remove impurities, and desiccated to remove water so as to control a water content to be below 0.1 wt. %.

B. Melting: the waste sheet of the polylactic acid, the waste film material of the polylactic acid, and the waste product of the polylactic acid substandard polylactic acid after the pretreatment was transported to a hopper of a twin screw extruder. A melt was extruded from the twin screw extruder and introduced into a pre-depolymerization kettle for chain scission treatment to obtain a polylactic acid melt.

C. Chain scission: the polylactic acid melt was added with a catalyst comprising stannous octoate, stannous lactate, and tin lactate at a weight ratio of 2:1:1 at a temperature of 180° C., and a weight ratio of the catalyst to the polylactic acid melt was controlled at 50/10000. Chain scission reaction was performed in stirring condition to break the molecular chain of the polylactic acid melt. After 4 hr of reaction, the number-average molecular weight of the polylactic acid melt in the kettle was decreased to below 2500.

D. Depolymerization: the polylactic acid melt after the chain scission was transported to a depolymerization system via a first delivery pump, and depolymerization reaction was conducted at a temperature of 220° C. at a vacuum of 0.1 MPa to yield crude lactide. A content of L-lactide in the crude lactide reached 90 wt. %.

E. Purification: the crude lactide obtained from the depolymerization was transported to a melt crystallization system via a second delivery pump. A refrigerant circulating pump of a dual falling film crystallizer was started. A circulating pump of a crude lactide was started. The temperature was decreased from 100° C. to 60° C. at a rate of 5° C./hr by a refrigerant of the crystallizer, and lactide began to be crystallized in the crystallizer. The crystallization was finished when a crystallized lactide accounted for 80 wt. % of a total weight of the crude lactide. The circulating pump of the crude lactide was stopped, and an uncrystallized solution residue was discharged. The refrigerant circulating pump of the crystallizer was stopped, and a heating medium circulating pump was started. The temperature was increased from 60° C. to 95° C. at a rate of 5° C./hr by a heating medium of the crystallizer, and then sweating treatment was performed. When a sweating solution reached 10 wt. % of the crystallized lactide, the sweating treatment was finished, and the sweating solution was discharged. A temperature of the heating medium was increased to 100° C., and crystals in the crystallizer were totally melted and discharged. A product after the crystallization had a content of 99.5 wt. % and an optical purity of 99.9%.

Example 3

A. Pretreatment of raw materials: a waste product of the polylactic acid and scraps of polylactic acid products was broken into particles having a diameter of 4 cm by a crusher, washed and filtrated to remove impurities, and desiccated to remove water so as to control a water content to be below 0.1 wt. %.

B. Melting: the waste product of the polylactic acid and the scraps of polylactic acid products after the pretreatment was transported to a hopper of a twin screw extruder. A melt was extruded from the twin screw extruder and introduced into a pre-depolymerization kettle for chain scission treatment to obtain a polylactic acid melt.

C. Chain scission: the polylactic acid melt was added with a composite catalyst comprising zinc lactate, stannous lactate, and butyl titanate at a weight ratio of 1:1:1 at a temperature of 250° C., and a weight ratio of the catalyst to the polylactic acid melt was controlled at 100/10000. Chain scission reaction was performed in stirring condition to break the molecular chain of the polylactic acid melt. After 5 hr of reaction, the number-average molecular weight of the polylactic acid melt in the kettle was decreased to below 2500.

D. Depolymerization: the polylactic acid melt after the chain scission was transported to a depolymerization system via a first delivery pump, and depolymerization reaction was conducted at a temperature of 220° C. at a vacuum of 0.098 MPa to yield crude lactide. A content of L-lactide in the crude lactide reaches 90 wt. %.

E. Purification: the crude lactide obtained from the depolymerization was transported to a melt crystallization system via a second delivery pump. A refrigerant circulating pump of a dual falling film crystallizer was started. A circulating pump of a crude lactide was started. The temperature was decreased from 100° C. to 60° C. at a rate of 5° C./hr by a refrigerant of the crystallizer, and lactide began to be crystallized in the crystallizer. The crystallization was finished when a crystallized lactide accounted for 80 wt. % of a total weight of the crude lactide. The circulating pump of the crude lactide was stopped, and an uncrystallized solution residue was discharged. The refrigerant circulating pump of the crystallizer was stopped, and a heating medium circulating pump was started. The temperature was increased from 60° C. to 95° C. at a rate of 5° C./hr by a heating medium of the crystallizer, and then sweating treatment was performed. When a sweating solution reached 10 wt. % of the crystallized lactide, the sweating treatment was finished, and the sweating solution was discharged. A temperature of the heating medium was increased to 100° C., and crystals in the crystallizer were totally melted and discharged. A product after the crystallization has a content of 99.6 wt. % and an optical purity of 99.9%.

Example 4

A. Pretreatment of raw materials: an unqualified polylactic acid was broken into particles having a diameter of 4 cm by a crusher, washed and filtrated to remove impurities, and desiccated to remove water so as to control a water content to be below 0.1 wt. %.

B. Melting: the unqualified polylactic acid after the pretreatment was transported to a hopper of a twin screw extruder. A melt was extruded from the twin screw extruder and introduced into a pre-depolymerization kettle for chain scission treatment to obtain a polylactic acid melt.

C. Chain scission: the polylactic acid melt was added with a composite catalyst comprising zinc lactate, zinc dust, and propionic acid at a weight ratio of 1:2:1 at a temperature of 190° C., and a weight ratio of the catalyst to the polylactic acid melt was controlled at 20/10000. Chain scission reaction was performed in stirring condition to break the molecular chain of the polylactic acid melt. After 1 hr of reaction, the number-average molecular weight of the polylactic acid melt in the kettle was decreased to below 2300.

D. Depolymerization: the polylactic acid melt after the chain scission was transported to a depolymerization system via a first delivery pump, and depolymerization reaction was conducted at a temperature of 200° C. at a vacuum of 0.098 MPa to yield crude lactide. A content of L-lactide in the crude lactide reaches 92 wt. %.

E. Purification: the crude lactide obtained from the depolymerization was transported to a melt crystallization system via a second delivery pump. A refrigerant circulating pump of a dual falling film crystallizer was started. A circulating pump of a crude lactide was started. The temperature was decreased from 100° C. to 60° C. at a rate of 5° C./hr by a refrigerant of the crystallizer, and lactide began to be crystallized in the crystallizer. The crystallization was finished when a crystallized lactide accounted for 80 wt. % of a total weight of the crude lactide. The circulating pump of the crude lactide was stopped, and an uncrystallized solution residue was discharged. The refrigerant circulating pump of the crystallizer was stopped, and a heating medium circulating pump was started. The temperature was increased from 60° C. to 95° C. at a rate of 5° C./hr by a heating medium of the crystallizer, and then sweating treatment was performed. When a sweating solution reached 10 wt. % of the crystallized lactide, the sweating treatment was finished, and the sweating solution was discharged. A temperature of the heating medium was increased to 100° C., and crystals in the crystallizer were totally melted and discharged. A product after the crystallization has a content of 99.6 wt. % and an optical purity of 99.9%.

While particular embodiments of the invention have been shown and described, it will be obvious to those skilled in the art that changes and modifications may be made without departing from the invention in its broader aspects, and therefore, the aim in the appended claims is to cover all such changes and modifications as fall within the true spirit and scope of the invention.

The invention claimed is:

1. A method for preparing a refined lactide from recovered polylactic acid, the method comprising:
    a) crushing recovered polylactic acid by a crusher, washing and filtrating the polylactic acid to remove impurities, and desiccating the polylactic acid to remove water;
    b) transporting the polylactic acid obtained in a) to a hopper of a twin screw extruder, extruding the polylactic acid from the twin screw extruder to yield a polylactic acid melt, and introducing the polylactic acid melt to a pre-depolymerization kettle;
    c) stirring the polylactic acid melt in the presence of a catalyst at a temperature of between 180 and 250° C. for carrying out a chain scission reaction to break molecular chains of the polylactic acid melt and to decrease a number-average molecular weight of the polylactic acid melt to below 5000;
    d) transporting the polylactic acid melt after the chain scission reaction to a depolymerization system via a first delivery pump, and conducting depolymerization reaction at a temperature of between 150 and 250° C. and at a vacuum between 0.1 and 0.09 MPa to yield a crude lactide; and
    e) transporting the crude lactide to a purification system via a second delivery pump, and crystallizing the purified lactide, whereby yielding a refined lactide wherein
    the catalyst in c) is a mixture of zinc lactate, zinc dust, and propionic acid; an amount of the catalyst is between 1/10000 and 100/10000 of the polylactic acid melt by weight; and
    the crude lactide in d) comprises L-lactide and D-lactide, a concentration of the L-lactide exceeds 85 wt. % of the crude lactide; and a concentration of the D-lactide is less than 2 wt. % of the crude lactide.

2. The method of claim 1, wherein the recovered polylactic acid is selected from the group consisting of a substandard polylactic acid, a waste sheet of the polylactic acid, a waste film material of the polylactic acid, a waste product of the polylactic acid, and scraps produced in processing polylactic acid products, and a mixture thereof.

3. The method of claim 1, wherein the recovered polylactic acid is particles of a diameter between 3 and 4 cm.

4. The method of claim 1, wherein a water content of the recovered polylactic acid is controlled at below 0.1 wt. %.

5. The method of claim 1, wherein the chain scission reaction in step c) lasts for between 1 and 5 hr.

6. The method of claim 1, wherein the number-average molecular weight of the polylactic acid melt after the chain scission reaction in step c) is decreased to between 2000 and 3000.

7. The method of claim 1, wherein the depolymerization system in step c) comprises: a circulating pump, a horizontal depolymerization kettle, and a wiped film evaporator.

8. The method of claim 1, wherein the temperature of materials in the depolymerization reaction is controlled at between 180 and 220° C.

9. The method of claim 1, wherein the vacuum in the depolymerization reaction in step c) is controlled at between 0.1 and 0.098 MPa.

10. The method of claim 1, wherein the purification system comprises a melt crystallization device, the melt crystallization device comprises: a circulating pump, a dual falling film melt crystallizer, and a lactide tank.

11. The method of claim 1, wherein the refined lactide in step e) has a lactide content exceeding 99.5 wt. % and an optical purity exceeding 99.5%.

* * * * *